United States Patent
Zhang et al.

(10) Patent No.: US 10,519,441 B2
(45) Date of Patent: Dec. 31, 2019

(54) USE OF MIRNA-214 INHIBITOR IN INHIBITING REGULATORY CELLS

(71) Applicant: JIANGSU MICROMEDMARK BIOTECH CO., LTD., Jiangsu (CN)

(72) Inventors: Chenyu Zhang, Beijing (CN); Ke Zeng, Beijing (CN); Yuan Yin, Beijing (CN); Xing Cai, Jiangsu (CN); Junfeng Zhang, Jiangsu (CN)

(73) Assignee: Jiangsu Micromedmark Biotech Co., Ltd., Jiangsu (CN)

( * ) Notice: Subject to any disclaimer, the term of this patent is extended or adjusted under 35 U.S.C. 154(b) by 0 days.

(21) Appl. No.: 15/108,285

(22) PCT Filed: Dec. 18, 2014

(86) PCT No.: PCT/CN2014/094247
§ 371 (c)(1),
(2) Date: Jun. 24, 2016

(87) PCT Pub. No.: WO2015/096659
PCT Pub. Date: Jul. 2, 2015

(65) Prior Publication Data
US 2016/0326525 A1    Nov. 10, 2016

(30) Foreign Application Priority Data

Dec. 27, 2013  (CN) .......................... 2013 1 0739044

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |

(Continued)

(52) U.S. Cl.
CPC .......... *C12N 15/113* (2013.01); *C12Q 1/6876* (2013.01); *C12N 2310/113* (2013.01); *C12Q 2600/106* (2013.01); *C12Q 2600/158* (2013.01)

(58) Field of Classification Search
CPC ...... A61K 48/00; C12N 15/11; C12N 15/113; C12N 2310/113; C12Q 1/6876; C12Q 2600/106; C12Q 2600/1158
See application file for complete search history.

(56) References Cited

FOREIGN PATENT DOCUMENTS

| | | |
|---|---|---|
| CN | 101641440 A | 2/2010 |
| CN | 102335189 A | 2/2012 |
| CN | 103370424 A | 10/2013 |

OTHER PUBLICATIONS

Yang et al. (Cancer Cell International, Jul. 8, 2013 vol. 13:68, pp. 1-10).*

(Continued)

*Primary Examiner* — Terra C Gibbs
(74) *Attorney, Agent, or Firm* — Kilpatrick Townsend & Stockton LLP

(57) ABSTRACT

Provided is a use of miRNA-214 inhibitor in inhibiting regulatory T cells (Treg cells). The microRNA-214 (miRNA-214) can promote Treg cells, and can assist tumors in immune escape. The experiments demonstrates that the inhibition of miRNA-214 can inhibit the growth of Treg cells, thus inhibiting the growth of tumors. Therefore, miRNA-214 can be used for developing an anti-tumour drug or a drug inhibiting immune response hyperactivity.

7 Claims, 8 Drawing Sheets

Specification includes a Sequence Listing.

(51) Int. Cl.
    *C12N 15/113*     (2010.01)
    *C12Q 1/6876*     (2018.01)

(56) References Cited

OTHER PUBLICATIONS

Walsh et al. (J Clin Invest 2006; 116:2521-2531).*
Penna et al. (The EMBO Journal, 2011 vol. 30:1990-2007).*
Yang et al. (Cancer Research, 2008 vol. 68:425-433).*
Zhou, X. Y. et al., "Selective miRNA disruption in T reg cells leads to uncontrolled autoimmunity," J. Exp. Med., vol. 205, No. 9, Aug. 25, 2008, pp. 1983-1991.
Zhao Xueyan et al., "Enhancement effects of miR-214 on invasive and metastatic ability of gastric cancer cell line SGC7901," Chinese Journal of General Surgery, Apr. 2012, vol. 21, No. 4, pp. 421-426.
Yin, Yuan et al., "Tumor-secreted miR-214 induces regulatory T cells: a major link between immune evasion and tumor growth," Cell Research, Sep. 16, 2014, vol. 24, pp. 1164-1180.
International Search Report issued in connection with corresponding International Application No. PCT/CN2014/094247 dated Mar. 23, 2015; 2 pages.

* cited by examiner

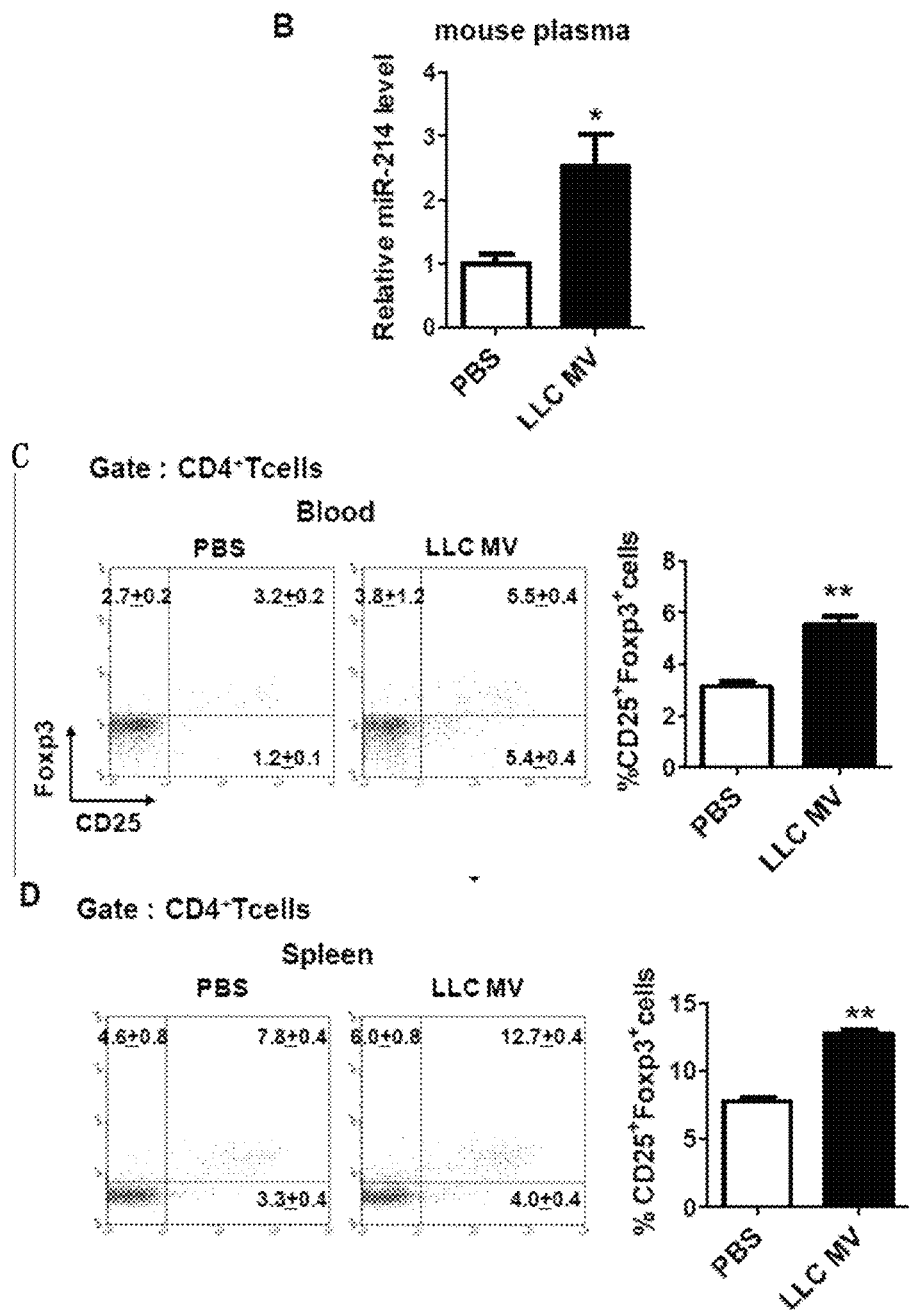
Fig. 2B-D

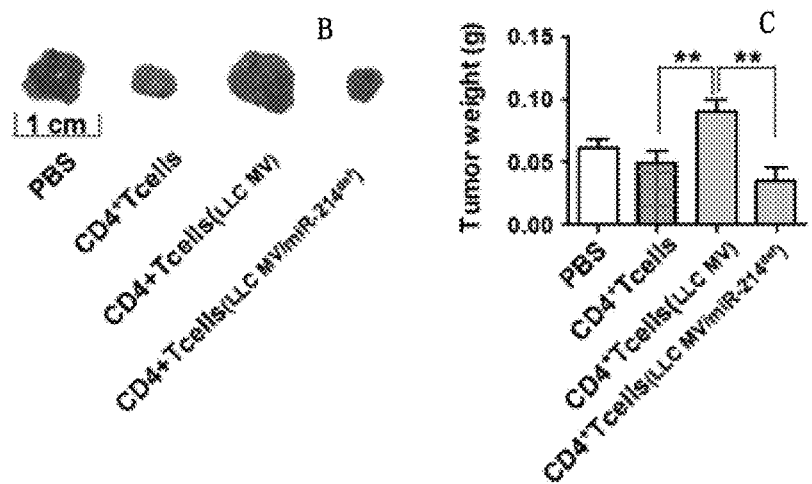
Fig. 5B-C
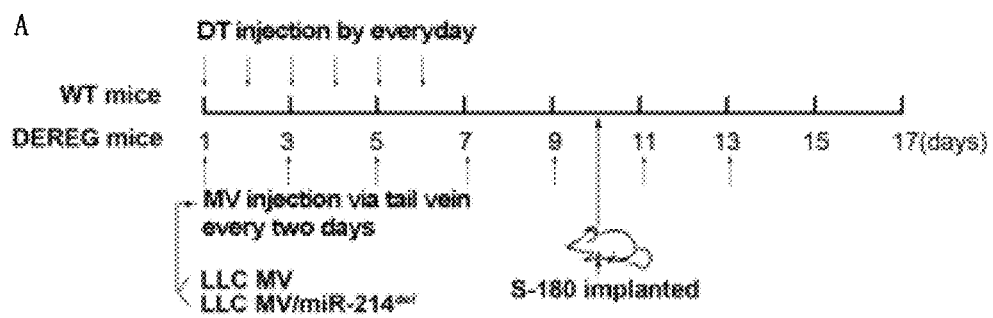
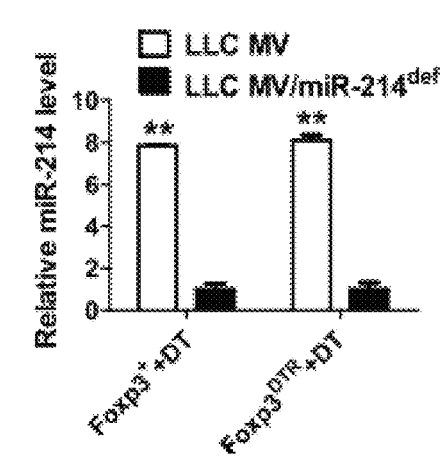
Fig. 6A-B

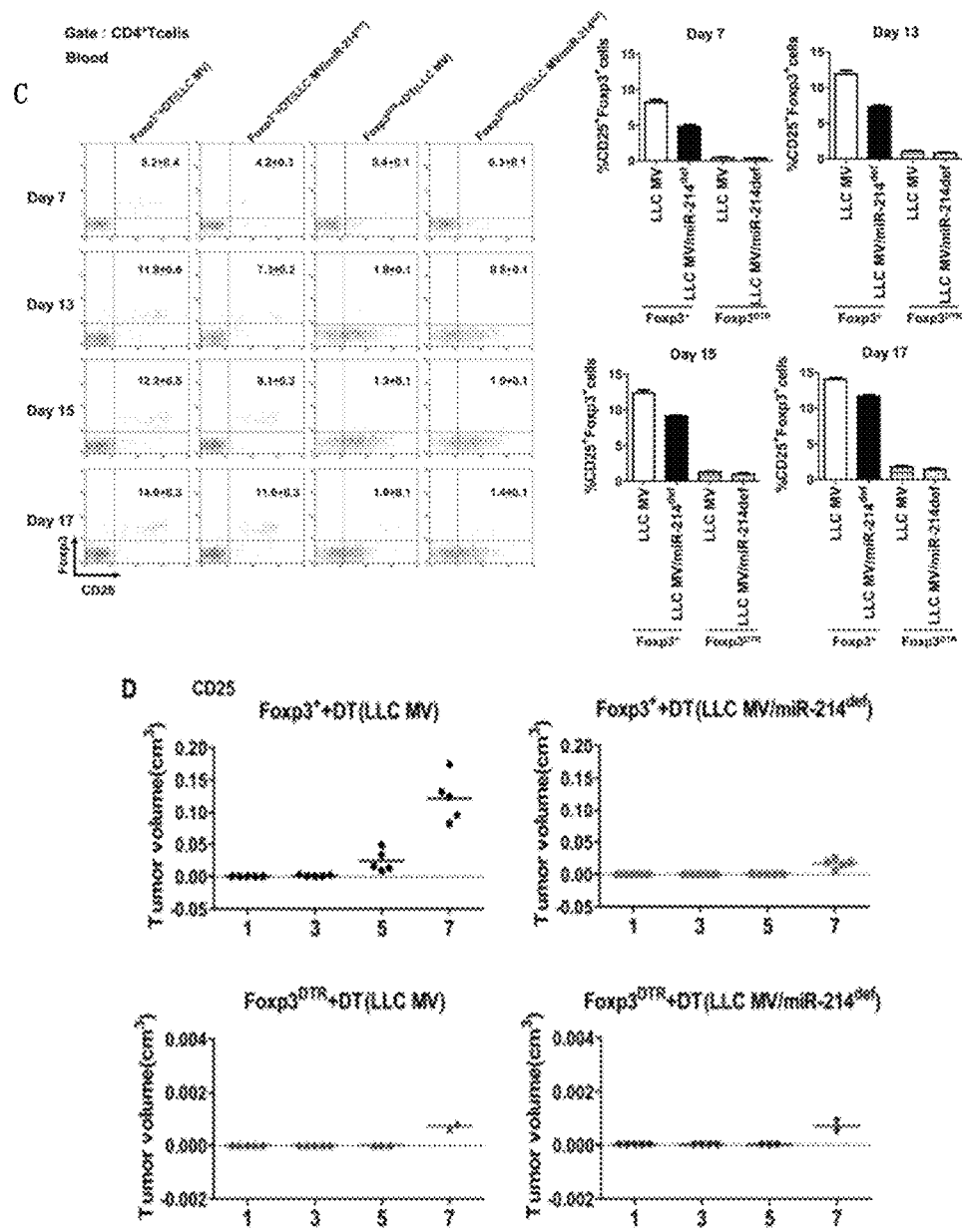
Fig. 6C-D

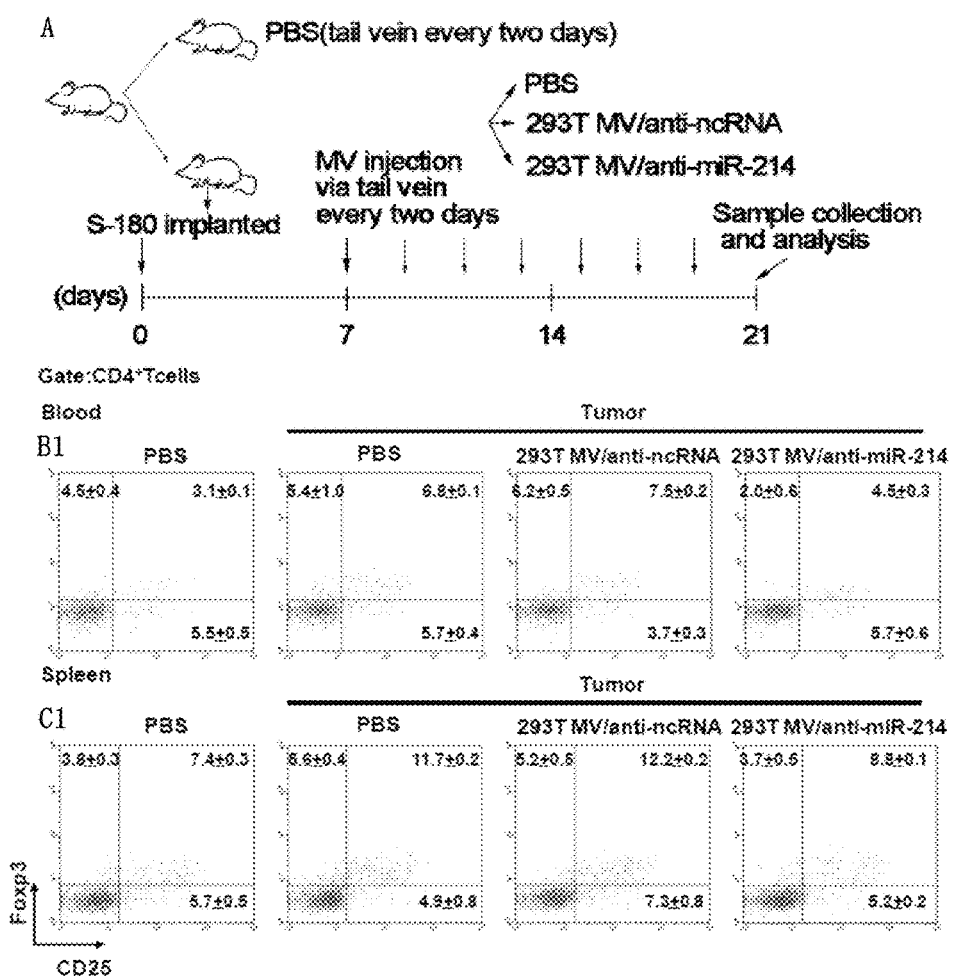
Fig. 7A、B1、C1

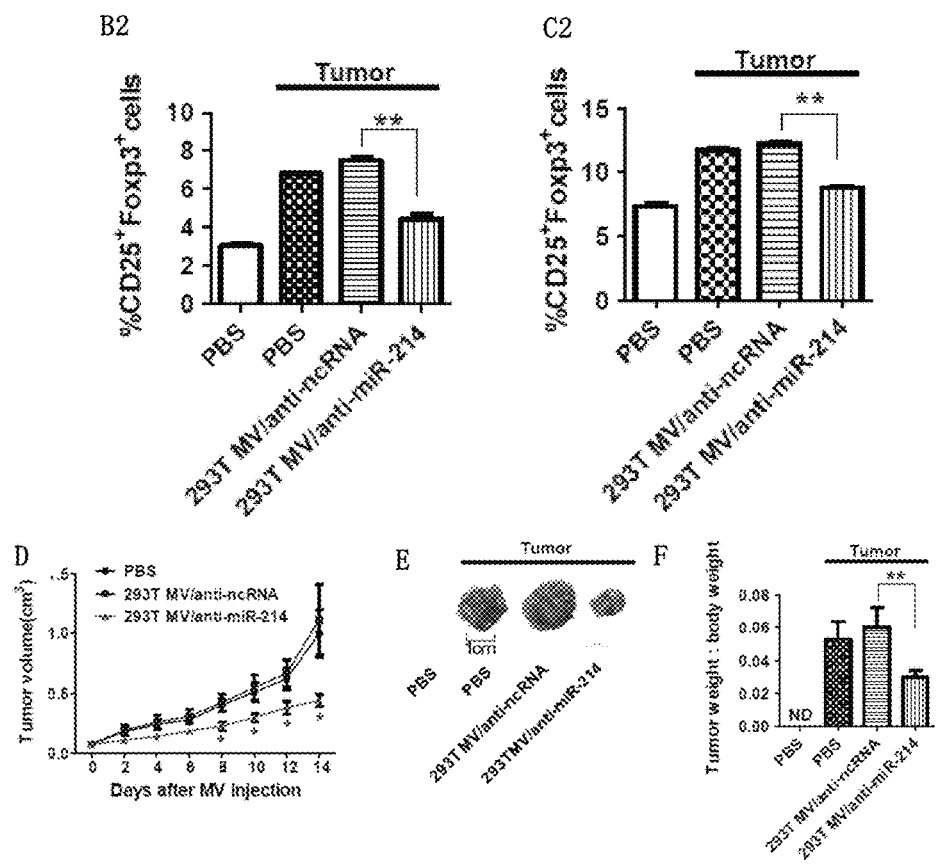
Fig. 7B2、C2、D-F

SEQUENCE LISTING

```
<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
acagcaggca cagacaggca gu                                              22

<210> SEQ ID NO 2
<211> LENGTH: 22
<212> TYPE: RNA
<213> ORGANISM: Homo sapiens

<400> SEQUENCE: 2
ugccugucua cacuugcugu gc                                              22
```

USE OF MIRNA-214 INHIBITOR IN INHIBITING REGULATORY CELLS

CROSS-REFERENCE TO RELATED APPLICATIONS

This application is a national phase application under 35 U.S.C. 371 claiming priority to PCT/CN2014/094247, filed Dec. 18, 2014, which application claims priority to CN201310739044.1, filed Dec. 27, 2013, the teachings of which are hereby incorporated by reference in their entireties for all purposes.

REFERENCE TO SUBMISSION OF A SEQUENCE LISTING AS A TEXT FILE

The Sequence Listing written in file P2016-0863seq.txt created on Oct. 17, 2018, 610 bytes, machine format IBM-PC, MS-Windows operating system, is hereby incorporated by reference in its entirety for all purposes.

TECHNICAL FIELD

The present invention pertains to the field of tumor treatment, specifically to the use of miRNA-214 inhibitors in the inhibition of regulatory T cells (Treg cells) and tumor immune evasion, and thereby the prevention or treatment of tumors.

BACKGROUND ART

MicroRNAs derive from the long strain RNA prime transcription products (pri-miRNA) with a length of about 1000 bp; the pri-miRNA molecules are cut in the nucleus by Drosha enzymes into miRNA precursors with a stem-loop structure and a length of about 60-80 nt. As the double-strand miRNA unfolds, the mature miRNA enters the RNA-induced silencing complex (RISC) and pairs completely or incompletely with the complementary mRNA, so as to degrade the target mRNA or prevent the expression thereof. The pri-miRNAs are transported into the cytoplasm and further cut into double-strand miRNAs with a length of 18-26 nt. As the double-strand miRNA unfolds, the mature miRNA enters the RNA-induced silencing complex (RISC) and pairs completely or incompletely with the complementary mRNA, so as to degrade the target mRNA or prevent the expression thereof.

Although microRNAs take only a small share of the cell total RNA, they take part in a series of important life processes, including early-stage embryo development, cell reproduction and cell death, cell apoptosis and fat metabolism, cell differentiation and gene expression regulation. It is common to observe in tumors irregularities of cell reproduction and apoptosis, therefore the irregular absence, mutation or over-expression of miRNAs are conjectured as being able to cause human diseases.

In the long history of evolution, the mammals have acquired a complicated system of self-evaluation and balancing in immune regulation, so as to ensure that the body can maintain a state of self-tolerance while offending the external antigens, of which many mechanisms are however until now not yet completely disclosed.

Recently it is proved with more and more evidences that miRNAs play an extremely important role in immune regulation and the development of immune cells, but only a relatively small number of specific miRNAs are disclosed as important regulators of the immune system. People know still little about the functions of miRNAs, especially in the tumor immune related field.

Therefore, it is an urgent need in the field of tumor treatment to learn about the functions of various miRNAs, so as to discover new medicines for tumor treatment.

CONTENT OF THE INVENTION

The present invention provides the use of miRNA-214 on regulatory T cells and tumor immune evasion.

In the first aspect of the present invention, provided is a use of inhibitors of miRNA-214 or precursor thereof for preparing a pharmaceutical composition for inhibiting Treg cells and thereby promoting T cells-induced immune responses.

In another preferred example, said miRNA-214 is originated from humans or non-human mammals; preferably, said non-human mammals are rats, mice.

In another preferred example, said inhibitors of miRNA-214 include anti-sense nucleotide sequences of miRNA-214 or the precursor thereof.

In another preferred example, said Treg cells include CD4+CD25+ Treg, CD4+ Th3, CD4+ Tr1, CD4+CD25+ Treg, or CD4+CD8+ Ts.

In another preferred example, said medical compositions comprise the inhibitors of miRNA-214 or the precursors thereof as active ingredients, and pharmaceutically acceptable carriers.

In another preferred example, said pharmaceutically acceptable carriers are selected from the group: water, saline solution, liposomes, lipids, proteins, protein-antibody complex, peptides, cellulose, nanogel, or the combination thereof.

In another preferred example, said inhibitors further inhibit the immune evasion of tumors.

In another preferred example, said tumors include colon cancer, hepatoma, gastric cancer, esophageal cancer, nasopharyngeal cancer, breast cancer, cervical cancer, fibroblastoma, myeloma, peripheral nerve sheath tumor.

In another preferred example, said inhibiting Treg cells comprises inhibiting differentiation of T cells into Treg cells, growth of Treg cells, or reproduction of Treg cells.

In the second aspect of the present invention, provided is a method for selecting candidate compositions which can be used as Treg inhibitors to prevent or treat tumors comprises following steps:

(a) adding a test composition into a cell culture system for a test group and detecting miRNA-214 expression and/or activity as well as Treg cells counts; adding no test composition into a cell culture system for a control group and detecting miRNA-214 expression and/or activity as well as Treg cells count wherein, if the miRNA-214 expression and/or activity of the test group is significantly lower than that of the control group and the Treg cells count of the test group is significantly less than that of the control group, it indicating that said test composition inhibits miRNA-214 or Treg cells, thereby preventing or treating tumors.

In another preferred example, further comprises a step (b) further testing an efficacy of the composition in (a) in preventing or treating tumor.

In the third aspect of the present invention, provided is a non-therapeutical method for inhibiting Treg cells in vitro by adding miRNA-214 inhibitors into a culture system so as to inhibit Treg cells and/or immune evasion of tumors.

In the fourth aspect of the present invention, provided is a method for preventing or treating tumors by inhibiting tumor evasion by administering a safe and effective dose of miRNA-214 inhibitors to a subject in need so as to prevent or treat tumor by inhibiting Treg cells and tumor evasion.

In another example, said subjects are mammals, preferably humans.

In another example, said subjects are cancer patients, and said cancers include colon cancer, hepatoma, gastric cancer, esophageal cancer, nasopharyngeal carcinoma, breast cancer, cervical cancer, fibroblastoma, myeloma and peripheral nerve sheath tumor.

In the fifth aspect of the present invention, provided is a use of an active ingredient, said active ingredient is selected from the following groups:

(a) microRNA-214 (miRNA-214) family, said miRNA-214 family includes miRNA-214 or modified derivatives of miRNA-214, miRNAs or modified miRNA derivatives with same or basically same functions as miRNA-214;

(b) precursor miRNAs, said precursor miRNAs can be processed into said miRNAs of (a) in a host;

(c) polynucleotides, said polynucleotides can be transcribed into the precursor miRNAs of (b) in a host, and then processed into the miRNAs of (a);

(d) expression vectors, said expression vectors contain the miRNAs of (a), or the precursor miRNAs of (b), or the polynucleotides of (c);

(e) agonists of the miRNAs of (a);

wherein, said active ingredient is used for preparing compositions to promote regulatory T cells.

In another preferred example, said active ingredient is used to prepare compositions to inhibit the immune response induced by T cells.

In another preferred example, said compositions comprise the active ingredient as said in claim 1 and pharmacy-acceptable carriers.

In another preferred example, said promotion of regulatory T cells includes the promotion of T cells differentiation into Treg cells, of T cells growth, and of Treg cells proliferation.

In another preferred example, said miRNA-214 has a nucleotide sequence as shown in SEQ ID NO.: 1 (ACAGCAGGCACAGACAGGCAGU).

In another preferred example, said active ingredient is used to prepare medical compositions for immune inhibition.

It shall be understood that, within the scope of the present invention, the aforesaid technical features and the technical features as specified in the following content (e.g., in the examples) can be combined with each other, so as to form new or more preferable technical strategy. For the economy of words, the combinations will not be listed herein one by one.

BRIEF DESCRIPTION OF THE DRAWINGS

FIG. 1A is the expression of miR-214 in the plasma and cellular microvesicles of s-180 tumor transplant model mice, 'normal' is the control group, 's-180' is the test group; FIG. 1B is the expression of miR-214 in the plasma and cellular microvesicles of LLC tumor transplant model mice, in which 'MV-free' is the control group, 'LLC MV' is the test group.

FIG. 2 shows the results of affect from LLC MVs on Treg. 'PBS' is the control group, 'LLC MV' is the test group. FIG. 2B shows the expression of miR-214 in the plasma of mice intravenously injected with LLC MV. FIG. 2C is the flow cytometry results of Treg cells in the whole blood of mice treated with LLC MV. FIG. 2D is the flow cytometry results of Treg cells in the spleen of mice treated with LLC MV.

FIG. 3A is the detailed experiment design chart, which shows: firstly LLC MVs are collected, and then C57BL/6J mice are intravenously injected with the LLC MVs (100 μL PBS containing 20 μg protein) once every other day and 7 rounds in all. On the 14th day, the mice are implanted with s-180 tumor ($10^6$ cells/mouse), and on the 24th day, the blood and tumor tissue samples are collected. FIG. 3B is the expression of miR-214 in the plasma of s-180 tumor transplant model mice. FIG. 3C is the tumor volume change curve of the mice pre-processed with LLC MVs. FIG. 3D is the actual volume image of the implanted tumor in the mice pre-processed with LLC MVs. FIG. 3E shows the weight of the implanted tumor in the mice pre-processed with LLC MVs.

FIG. 4A shows the flow cytometry results of mice Treg cells. FIG. 4B is the bar graph for the counting results of mice Treg cells. Control presents the control group; 5 LLC MV, 10 LLC MV and 10 LLC MV/miR-214$^{def}$ present the test groups. FIG. 4A shows the mean value±standard error mean (SEM) of 5 experiments.

FIG. 5 shows the volume and weight changes of tumor in mice treated with different MVs and implanted with sarcoma S-180 cells. FIG. 5B shows the volume of tumors, in which 'PBS' represents the control group, and '$CD4^+$ T cell', '$CD4^+$ T cell (LLC MV)', '$CD4^+$ T cell (LLC MV/miR-214$^{def}$)' represent the test groups. FIG. 5C shows the weight of tumors, which is the same as that in FIG. 5B.

FIG. 6 shows the miR-214 expression in CD4+ T cells and Tregs cell count in the peripheral blood of, and the volume of tumors from Foxp3DTR mice treated with LLC MVs and LLC MV/miR-214$^{def}$, and wild type mice. FIG. 6A shows the experiment flow chart of example 5, which shows that, firstly Tregs deficient (Foxp3$^{DTR}$) model mice are constructed; then Foxp3$^{DTR}$ model mice and wild type mice are treated every other day and for 2 weeks in a row with diphtherotoxin; meanwhile, Foxp3$^{DTR}$ model mice and wild type mice are treated with LLC MVs or LLC MV/miR-214$^{def}$; on the 10th day, the mice are injected with S-180 sarcoma cells; on the 17th day, the mice are sacrificed, and the samples thereof are collected. FIG. 6B shows the qRT-PCR results on the miR-214 expression in the spleen $CD4^+$ cells of Foxp3$^{DTR}$ and Foxp3$^+$ mice. FIG. 6C shows the flow cytometry results of the Tregs cell count in the whole blood of Foxp3$^{DTR}$ and Foxp3$^+$ mice. FIG. 6D shows the sarcoma volume of Foxp3$^{DTR}$ mice and wild type mice treated with LLC MVs and LLC MV/miR-214$^{def}$. *, $p<0.05$; **, $p<0.01$.

FIG. 7 shows the changes of CD4+ and Tregs in the whole blood and spleen of mice implanted with sarcoma S-180 and treated with different MVs, and the tumor growth situation thereof. Mice not implanted with sarcoma S-180 (PBS) and sarcoma S-180 model mice treated with saline solution (PBS) are the control groups; sarcoma S-180 model mice injected with 293TMV/anti-miR-214 (293TMV/anti-miR-214) and sarcoma S-180 model mice injected with 293TMV/anti-ncRNA (293TMV/anti-ncRNA) are the test groups. FIG. 7A shows the experiment flow chart of example 6, which shows that, firstly sarcoma S-180 implanted model mice are constructed; then group experiments are carried out, i.e., mice of test groups and control groups are treated with different MVs, and then samples are collected and detected. FIG. 7B-C shows that anti-miR-214 ASOs can inhibit the proliferation of $CD4^+CD25^{high}Foxp3^+$ Tregs. In which, FIGS. 7B1 and 7C1 shows that the Tregs count reduces significantly in the whole blood (B1) and spleen (C1) from sarcoma S-180 mice injected with 293TMV/anti-miR-214; 7B2 and 7C2 shows the Tregs count by flow cytometry analysis in the whole blood (B2) and spleen (C2) of mice. FIG. 7D-F shows the tumor growth situation of mice in all groups after being injected for 14 days with MVs.

PARTICULAR EMBODIMENTS

Figure 1:
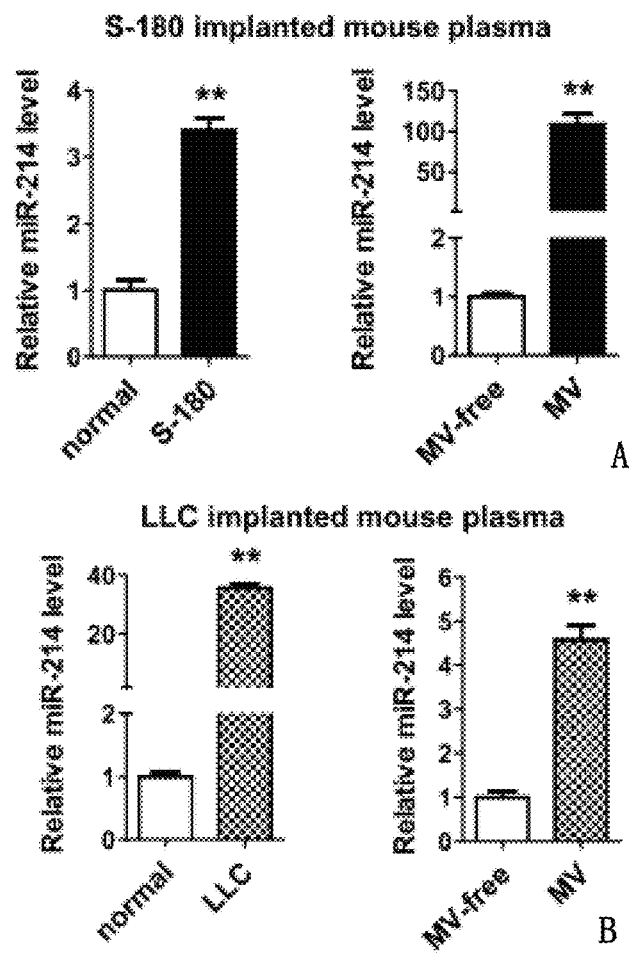
FIG. 1 shows the expression level of miR-214 in the plasma and cellular microvesicles of s-180 tumor transplant model mice and LLC transplant model mice.

The inventors were surprised to find in their wide and in-depth researches that, miRNA-214 inhibits the differentiation of T cells into immune response T cells, depresses the immune response, thereby assisting the immune evasion of tumor cells through promoting the differentiation of T cells into Treg cells, and the proliferation and activity thereof. The inventors has proved with experiments that, through the inhibition of miRNA-214, the Treg cells can be inhibited, and the differentiation of T cells into immune response T cells can be promoted, thereby inhibiting the immune evasion of tumors and achieving the goal of tumor prevention and/or treatment. The present invention is completed on this basis.

T Cells

Being the main component of lymph cells, T cells participate in cell immune and perform multiple biological functions, such as directly killing target cells, assisting or inhibiting the antibody production of B cells, and responding to specific antibodies and mitogens, and etc. They are valiant warriors produced by the bodies to fight against diseases, infections and tumors. The immune response triggered by T cells is cell immune, whose effect mechanism being of two kinds: to specifically combine with target cells, and destruct the target cell membrane, resulting in the direct killing of the target cells; and to release lymphokines, resulting the amplification and strengthening of the immune effect.

According to their functions and surface markers, T cells can be divided into many categories. The widely accepted T cells categorization at present is as follows:

Cytotoxic T cells: to eliminate the infected cells. These cells function as 'killers' or cytotoxins, since they can kill the target cells, i.e., the infected cells, in which particular antigen reactions take place. They are also called Natural Killer T cells (NK cells). The main surface marker of cytotoxic T cells is CD8. The $CD8^+$ T cell expresses CD8 on its surface and can participate in the immune response through the direct combination of MHCI with antigens.

Helper T cells: The helper T cell plays a role in the intermediate process of immune reaction, i.e., activating the other types of immune cells that trigger direct immune reactions through proliferation and spreading. The main surface marker of helper T cells is CD4.

Helper T cells regulate or 'assist' the performance of other lymph cells. They are the known target cells of HIV, being rapidly down-regulated at the occurrence of AIDS. The CD4+ T cell expresses CD4 on its surface and is activated by the peptide antigen reaction induced with MHC (major histocompatibility complex) II. Once activated, they can secret cytokines and thereby regulate or assist the immune reaction.

Regulatory T cells, Tregs: They are responsive for the regulation of immune reaction. Usually they play the important role of maintaining self-tolerance and avoiding the harm on bodies by over immune response. There are many types of regulatory/inhibiting T cells.

Memory T cells: They play an important role in the secondary immune response. Much of them is still unknown, due to that they don't have specific surface markers.

Until now, many miRNAs that function as T cell inhibitor are discovered, such as miRNA-144 and miRNA-181. These miRNAs are important for the prevention and treatment of autoimmune diseases.

Regulatory T Cell, Treg

Regulatory T cells, Tregs, are a type of T cells with a unique immune regulation function. They are important in aspects including tumor immune, anti-infection immune, immunopathogenesis, implant tolerance, inhibition of auto-immune reaction and immune balance maintenance.

Treg cells perform in vivo and in vitro regulatory functions. According to their different surface markers, cytokines secreted and action mechanisms, Treg cells can be divided into many subtypes including $CD4^+$ Th3, $CD4^+$ Tr1, $CD4^+CD25^+$ Treg, $CD4^-CD8^+$ Ts and NKT (Natural Killer T cells). Among the various subtypes of Tregs, $CD4^+CD25^+$ Tregs take a very important place. They bear two function characteristics, i.e, immune incapability and immune inhibition. Their immune incapability is shown by that, they remain at the non-responsive state and do not secret IL-2 under the single stimulation of high concentration IL-2, solid phase package, soluble anti-CD3 monoclonal antibody, or the combined treatment of anti-CD3 and anti-CD28 monoclonal antibody, meaning that $CD4^+CD25^+$ Treg cells show incapability to all conventional experimental stimulants of T cell receptors (TCR). Their immune inhibition is shown by that, they can strongly inhibit the activation, proliferation and functioning of $CD4^+$ and $CD8^+$ T Effector cells, and this immune inhibition is not limited by MHC.

$CD4^+CD25^+$ Treg cells are a group of cells that specialized in inhibition. They express CD4, CD25, cytotoxic T lymphocyte associated antigen-4 (CTLA-4), glucocorticoid induced tumor narcosis factor receptor (GITR) and forkhead/winged helix transcription factor (Foxp3), and etc. The transcription factor Foxp3 is closely related with the emergence, development and functioning of $CD4^+CD25^+$ Treg cells, and the expression of Foxp3 is seen as the specific marker of $CD4^+CD25^+$ Treg cells. The Foxp3 gene of mice is located at chromosome XA1.1, with a full length of 30858 bp, and the protein encoded comprises 431 amino acids. In thymus it is preferentially expressed at the $CD4^+CD25^+CD8^-$ T thymocytes, and in the peripheral, at the $CD4^+CD25^+$ Treg cells. In the Foxp3 deficient mice, an Immunodysregulation Polyendocrinopathy Enteropathy X-Linked (IPEX) Syndrome is caused by the absence and deficiency of $CD4^+CD25^+$ Treg cells, with the syndrome of uncontrolled activation and proliferation of $CD4^+$ T cells. In mice, Foxp3 is mainly expressed at $CD4^+$ T lymphocytes and is closely related with the emergence and function development of $CD4^+CD25^+$ Treg cells. The transfection of the Foxp3 gene carried by a retrovirus into $CD4^+CD25^+$ T cells not activated by antigens brings the CD25⁺ T cells with the similar phenotype and functional characteristics as CD4⁺CD25⁺ Treg, including the capability of in vitro proliferation, the down-regulation of IL-2 secretion, the up-regulation of the function relating surface markers, such as CD25, CTLA-4, GITR and CD103, and the capability to inhibit the proliferation of CD4⁺CD25⁺ Effector T cells and the secretion of IL-2 in a cell contact dependent way.

Treg cells participate in the immune evasion of tumors and are therefore very important in the aspect of immune balance. They are usually up-regulated when the body is in a tumor state. Being able to identify the TCR autoantigen peptide presented by the MHC molecules of their target cells and then perform certain functions of immune inhibition, they are a T cells subtype specified in immune inhibition, maintaining self-tolerance through down-regulating the immune response level to external and internal antigens.

The mechanism of Treg cell up-regulation in the tumor patients is as follows:

(1) Some cytokines secreted by tumor tissues can directly transform the CD4⁺CD25 T cells into CD4⁺CD25⁺ Tregs;

(2) Tumor cells can express CCL22 chemokines, guiding the CD4⁺CD25⁺ Tregs, which express the chemokine C-C-motif Receptor 4 (CCR4) and chemokine C-C-motif Receptor 8, to migrate into the micro environment of tumors;

(3) Tumor tissues release bountiful tumor-associated antigens (TAAS), which can be identified by tolerogenic dendritic cells, such as pDC or imDC, and then presented to Treg cells for identification, causing the activation and proliferation of Treg cells;

(4) Being stimulated by the tumor antigens, Treg cells express lymphocyte homing molecules CCR7 and CD62L, returning to lymphonodi from the peripheral blood, and accumulate rapidly through cell division.

Through the mechanism above, the specific immune inhibition caused by tumor antigens and induced by Tregs takes place.

The two main effect places of tumor immune inhibition by Tregs are: 1. In the tumor-draining lymphonodi, where excessively proliferating Treg cells specifically inhibit the proliferation of effector cells in the same lymphonodus; 2. In tumor tissues, where the up-regulated Treg cells inhibit the tumor cell killing effector T cells in TIL.

The molecular pathways of Tregs' inhibition effect mainly include:

(1) To inhibit the functioning of effector cells in the CTLA4 dependent way of direct cell contact inhibition;

(2) To inhibit the activation and proliferation of CD4⁺ T cells, or CD8+ effector cells and their precursors through secreting the inhibiting cytokines including TGF-β or IL-10;

(3) To inhibit the activation and proliferation of CD4⁺ T cells through affecting the APC to promote the metabolism of tryptophane;

(4) To form a micro environment that can transform the effector cells into immune inhibition cells, letting a part of CD4⁺CD25 T cells be induced by CD4⁺CD25⁺ Tregs and secret TGF-β or IL-10.

Making use of this kind of local micro environment, Treg cells can further disturb the proliferation, cytokine secretion and cytotoxic functioning of CD8⁺ T cells. Meanwhile, the increase of Treg cells can promote tumor growth and inhibit the tumor immune effect. Each phase of immune response is intervened by the Treg cell induced immune inhibition. CD4⁺CD25⁺ Tregs play an important role in the occurrence and progression of tumors.

Microvesicles

Microvesicles are vesicular bodies with bi-layer lipid membrane. They are secreted by cells and range 10-500 in size. They were firstly reported in 1967, that they originated from platelets and contained vesicles, were named as 'platelet dust' and functioned as coagulation promoters. The following studies in vitro found that, endothelial cells, vascular smooth muscle cells, leukocytes, lymphocytes and erythrocytes could all secret microvesicles (cellular). According to their different origins, microvesicles can be divided into two types: exosomes and shedding vesicles. Exsomes are driven out through multivesicular bodies (MVBs) by cells under stimulation, while shedding vesicles are directly sprouted from cell surface. Presently shedding vesicles from different cells are given different names, for example, these from neutrophile granulocytes and monocytes are called ectosomes, and from platelets, microparticles. The membrane components of microvesicles are mainly lipids and proteins, whose types are decided by their origin cells.

The inventors discovered that microvesicles are ideal drug carriers thanks to their high biological compatibility, since they originate from living beings. They can high-efficiently and specifically deliver miRNAs, such as the microRNA-214 family. Said microRNA-214 family includes: miRNA-214 or modified miRNA-214 derivatives, microRNAs with ugccugucuacacuugcugugc (SEQ ID NO.: 2) as the core sequence, a length of 18-26 nt, and functioning in the same or substantially the same way as miRNA-214, and modified derivatives thereof.

Specifically, the inventors discovered that, microvesicles are a type of biological vesicular carriers with high efficiency and strong specificity of delivery in vivo; the membrane surface components (including specific surface receptors and membrane lipid structure) of microvesicles release by different cells are identical to the plasma membrane components of their origin cells. Carrying the surface proteins or membrane lipid structure specific to their origin cells, microvesicles are therefore highly compatible to their target cells. Meanwhile, containing proteins essential for the functioning of the miRNA-214 family, microvesicles can deliver the miRNA-214 family high-efficiently and selectively into target cells (tissues), so as to significantly improve the regulation efficacy of the miRNA-214 family. Microvesicles (referring to all the membrane lipid vesicular structure with the microvesicular characteristics, including exosomes and shedding vesicles secreted by all kinds of cells) can elevate the specificity, target rate and stability of the miRNA-214 family delivery. The miRNA-214 family secreted by tumors are probably enveloped in the tumor-secreted microvesicles and participate in the regulation of signal conduction between tumors and immune cells, regulating the functioning of immune cells and assisting the immune evasion of tumors.

MiRNAs and Precursors Thereof

The present invention provides a type of miRNA relating to the immune evasion of tumors. As used herein, said 'miRNA' refers to a type of RNA molecules that can be processed with the transcription product that can turn into the miRNA precursors. Mature miRNAs usually comprise 18-26 nucleotides (nt) (more particularly, 19-22 nt), not excluding other numbers of nucleotides. The miRNAs can usually be detected with Northern blotting.

Human-originated miRNAs can be isolated from human cells. As used herein, 'isolated' refers to that a substance is isolated from its original environment (if the substance is a natural substance, its original environment is the natural environment). For example, the polynucleotides and polypeptides in a living cell are not isolated and purified in the natural state, but the same polynucleotides and polypeptides are isolated and purified when they are isolated from the other substances co-existing in the natural state.

MiRNAs can be processed with precursor miRNAs (pre-miRNAs). Said pre-miRNAs can fold into a stable stem-loop (hairpin) structure, of which the length is usually within 50-100 bp. Said pre-miRNA can fold into a stable stem-loop structure, and the two sides of the stem part of said stem-loop structure comprise two sequences that are substantially complementary. Said pre-miRNA can be naturally occurring or artificially synthesized.

The pre-miRNA can be cut to generate miRNA, and said miRNA may be substantially complementary to at least a portion of the sequence of the mRNA encoding the gene. As used herein, 'substantially complementary' means that the nucleotide sequence is sufficiently complementary and can act upon each other in a predictable manner, e.g., forming a secondary structure (such as a stem-loop structure). Generally, at least 70% of nucleotides in two 'substantially complementary' nucleotide sequences are complementary; preferably, at least 80% of nucleotides are complementary; more preferably, at least 90% of nucleotides are complementary; and further preferably, at least 95% of nucleotides are complementary, e.g., 98%, 99% or 100%. Generally, there are at most 40 non-matched nucleotides between two sufficiently complementary molecules; preferably, there are at most 30 non-matched nucleotides; more preferably, there are at most 20 non-matched nucleotides; and further preferably, there are at most 10 non-matched nucleotides, e.g., there are 1, 2, 3, 4, 5 or 8 non-matched nucleotides.

As used herein, the 'stem-loop' structure, also known as the 'hairpin' structure, refers to a nucleotide molecule which can form a secondary structure comprising of a double-stranded region (stem) comprising of two regions (in a same molecule) of this nucleotide molecule, with the two regions being at two sides of the double-stranded part; and the structure further comprises at least one 'loop' structure, comprising of non-complementary nucleotide molecules, i.e., a single-strand region. Even if the two regions of the nucleotide molecule are not fully complementary, the double-strand part of the nucleotide can also maintain the double-stranded form. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-strand region of the stem-loop structure. The stem-loop structure is commonly known by the skilled person in the art. Usually when being given a nucleic acid with nucleotide sequence of the first structure, a skilled person in the art can determine whether the nucleic acid can form the stem-loop structure.

The miRNA of the present invention refers to the micro-RNA-214 family, and said miRNA-214 family includes: miRNA-214 or modified miRNA-214 derivatives, which perform the same or basically the same functions as miRNA-214.

In another preferred example, said miRNA is originated from humans or non-human mammals; preferably, said non-human mammals are rats, mice. The sequences of miRNA-214 family from murines are identical to that from humans. Said 'with the same or basically the same functions as miRNA-214' refers to that ≥40%, ≥50%, ≥60%, ≥70%, ≥80%, ≥90% of the immune auto-inhibition function of miRNA-214 remains.

The present invention also includes miRNA varieties and derivatives. Besides, miRNA derivatives in the general sense can also include miRNA varieties. n ordinary skilled person in the art can modify miRNA-214 in a conventional way, and the modification methods include (but are not limited to): methylation, alkylation, glycosylation (such as modification with 2-methoxy-glycosyl, alkyl-glycosyl and glyco-conjugate, and etc.), nucleination, and modification with peptides, lipids, halogens and nucleins (such as 'TT' modification), and etc.

Pharmaceutical Compositions and Administration Methods Thereof

As used herein, the term 'effective amount' or 'effective dose' refers to the amount, with which a composition can take effect on and be accepted by humans and/or animals.

As used herein, the term 'pharmaceutically acceptable ingredient' refers to an ingredient that is applicable on humans and/or mammals without excessive adverse side effects (such as toxicity, stimulation and allergic reaction), i.e., ingredient with sensible benefit/risk ratio. The term 'pharmaceutically acceptable carrier' refers to the carrier for the effect ingredient, including all sorts of excipients and diluents.

The pharmaceutical composition of the present invention comprises the active ingredient of the present invention of the safe effect amount and a pharmaceutically acceptable carrier. The carriers include (but are not limited to): saline water, buffer, glucose, water, glycerol, ethanol, and a combination thereof. Generally, a pharmaceutical preparation shall match with the form of administration, and the dosage form of the pharmaceutical composition of the present invention can be injection, oral preparation (tablet, capsule, or oral liquid), transdermal agent, or sustained release agent. For example, preparation is performed with a conventional method using physiological saline or an aqueous solution containing glucose and other adjuvants. Said pharmaceutical composition is preferably produced under sterile conditions.

The effective amount of the active ingredient of the present invention may vary depending on the mode of administration and the severity of the disease to be treated. A person skilled in the art could determine the selection of the preferred effective amount depending on various factors (e.g., by clinical trials). Said factors include, but are not limited to, the pharmacokinetic parameters of said active ingredient, e.g., bioavailability, metabolism, half-life, etc.; and the severity of the patient's disease to be treated, the patient's weight, the patient's immune state, the administration route, etc. Generally, when the active ingredient of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered on one day, or the dosage can be proportionally reduced.

In the present invention, said pharmaceutically acceptable carriers include but are not limited to: water, saline solution, liposomes, lipids, proteins, protein-antibody complex, peptides, cellulose, nanogel, or the combination thereof. The choice of carriers should match the mode of administration, which is well known to an ordinary person skilled in the art.

The miRNA-214 of the present invention can be used to prepare pharmaceutical composition for immune inhibition. Said pharmaceutical composition can be applied to treat diseases relating to immune hyperfunction.

And miRNA-214 inhibitors can be used to prepare pharmaceutical compositions for the inhibition of tumor immune evasion, in which, the miRNA-214 inhibitors take effect on Tregs, inhibiting the differentiation, proliferation and activation of Tregs.

The Advantages of the Present Invention Include

1. The miRNA-214 of the present invention takes effect on Treg cells, being able to promote the differentiation and proliferation of Treg cells and thereby to inhibit T cells, which are for the immune effect;
2. The miRNA-214 and its precursor of the present invention can be used to inhibit the immune response, so as to treat auto-immune diseases caused by immune hyperfunction;
3. The miRNA-214 inhibitors of the present invention can inhibit Treg cells, thereby inhibiting the tumor immune evasion assisted by Treg cells.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbour Laboratory Press, 1989), or the conditions recommended by the manufacturer are followed. All percentages and portions are of weight unless otherwise indicated.

Example 1 Construction of Tumor Transplant Model Mice

Firstly tumor transplant model mice are constructed using mice sarcoma S-180 cells (Cell Bank, China Academy of Sciences) and mice Lewis lung cancer cells (LLC) (Cell Bank, China Academy of Sciences); secondly plasma and microvesicles (MVs) of all tumor transplant model mice are collected; then the miR-214 expression in the plasma and MVs of tumor transplant model mice is detected with Real time-PCR.

1.1 To construct sarcoma S-180 cell transplant model mice and Lewis lung cancer cell (LLC) transplant model mice C57BL/6J mice are adopted and divided into 3 groups:
i. The control group: C57BL/6J mice treated with 100 ul physiological saline through hypodermic injection;
ii Sarcoma S-180 cell transplant model mice: the model mice are constructed with C57BL/6J mice treated with sarcoma S-180 cells (100 ul, $10^6$ cells/mouse) through axillary hypodermic injection;
iii Lewis lung cancer cell (LLC) transplant model mice: the model mice are constructed with C57BL/6J mice treated with LLC cells (100 ul, $10^6$ cells/mouse) through axillary hypodermic injection.

1.2 Methods for the collection and separation of the plasma and microvesicles (MVs) of tumor transplant model mice The plasma and microvesicles (MVs) of tumor transplant model mice are separated with the differential centrifugation method.

Cell and tissue debris are centrifuged at 300×g, 1,200×g, and 10,000×g, the supernatant is collected and centrifuged at 110,000×g for 70 minutes. Then the precipitation is suspended with PBS and FBS-free culture medium, and the supernatant is discarded. All the centrifugation is carried out at the temperature of 4° C.

1.3 To detect the miR-214 expression with Real time-PCR in the plasma and MVs in tumor transplant model mice The total RNA in the plasma and MVs in tumor transplant model mice is extracted with the TRIzol method. The expression of miR-214 in the plasma and MVs of tumor transplant model mice is detected with the Real time-PCR method (Taqman small molecule probe).

1 μl total RNA is transcribed into cDNA with AMV anti-transcriptase, and stem-loop structured anti-transcription primer. Then the expression of miR-214 in the plasma and MVs of tumor transplant model mice is detected with the TaqMan PCR kit and Applied Biosystems 7900 PCR system. All experiments include negative control and are repeated 3 times. Ct is determined after the reactions with the set threshold value. To accurately detect the expression of subject miRNAs, several known miR oligonucleotides of fixed content are treated with the similar steps as control. Then the expression of each miRNA is determined with the standard curve. Since the content of U6 snRNA in MVs is relatively small, and no research has been made on the relating house-keeping genes, the miRNA content in MVs can therefore only be determined with the total protein content as the standard.

The detailed results are shown in FIG. 1.

It can be seen from FIG. 1A that, being compared with the control group, the expression of miR-214 in the test group (S-180), i.e., in the plasma of s-180 tumor transplant model mice is increased to 3.5 times of the control group (normal).

With MV-free as the control group, being compared with the control group, the expression of miR-214 in the test group (MV), i.e., in the MVs of s-180 tumor transplant model mice is increased to 130 times of the control group (MV-free).

It can be seen from FIG. 1B that, being compared with the control group, the expression of miR-214 in the test group (LLC), i.e., in the plasma of LLC tumor transplant model mice is increased to 3.5 times of the control group (normal).

With MV-free as the control group, being compared with the control group, the expression of miR-214 in the test group (MV), i.e., in the MVs of LLC tumor transplant model mice is increased to 4.5 times of the control group (MV-free).

In summary, being transplanted with S-180 and LLC cells, the expression of miR-214 in the plasma of tumor transplant model mice is significantly increased, and the increased miR-214 mainly exist in MVs.

Example 2 LLC MVs Promote Treg Proliferation and Tumor Growth

Figure 2A:
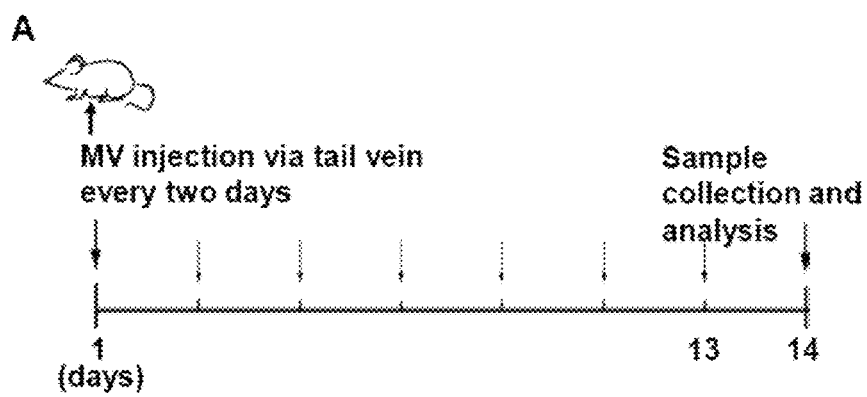
FIG. 2A is the detailed experiment design chart, which shows: firstly LLC MVs are collected, and then C57BL/6J mice are intravenously injected with the LLC MVs (100 μL PBS containing 20 μg protein) once every other day and 7 rounds in all. On the 14th day, the whole blood and T cells in spleen of the mice are collected, and therefrom blood and spleen samples are prepared.

Experiment group 1: firstly LLC MVs are collected and then intravenously injected to C57BL/6J mice. On the 14th day, the whole blood, T cells in spleen of mice are collected, as well as blood and spleen samples; the miR-214 expression in plasma is detected with Real-time PCR, and the $CD4^+CD25^{high}Foxp3^+$ cell count in the whole blood and spleen of mice in each group is detected with eBiosience Treg Flow Detection Kit (eBioscience) on a flow cytometry. The specific experiment design chart is shown in FIG. 2A.

Experiment group 2: LLC MVs are collected and then intravenously injected to C57BL/6J mice. On the 14th day, the mice are transplanted with s-180 tumor, and on the 24th day, the blood and tumor tissue samples are collected; then the miR-214 expression in plasma is detected with Real-time PCR; the size and weight of tumor tissues are also detected. The specific experiment design chart is shown in FIG. 3A.

2.1 The separation and collection of mice whole blood and MVs, and the specific operation thereof is as described in Example 1.

2.2 The miR-214 expression in plasma is detected with Real-time PCR, and the specific operation thereof is as described in Example 1.

2.3 The $CD4^+CD25^{high}Foxp3^+$ cell count in the whole blood and spleen of mice in each group is detected with eBioscience Treg Flow Detection Kit (eBioscience) on a flow cytometry.

The specific operation steps include:

1) The cells are prepared into cell suspension of $10^6$/ml with buffer;

2) 100 ul cells are taken, labeled with Fc (1 ug/sample) and sealed for 15 minutes at 4° C.;

3) The cells are labeled with CD4 (0.125 µg/sample) and CD25 (0.06 µg/sample) and then cultured at 4° C. for 30 minutes;

4) The cells are washed with buffer, and then the cell membrane is permeated with fixed film breaking agent for 30 minutes to 18 hours at 4° C.;

5) The cells are washed after permeation with permeation buffer and then labeled with antibodies of Foxp3 (0.5 µg/sample), and then cultured at 4° C. for 30 minutes;

6) The cells are washed with permeation buffer and suspended with buffer, and then detected on a flow cytometry;

7) The $CD4^+CD25^{high}Foxp3^+$ cell count in the whole blood and spleen of each group is detected.

2.4 Detection of the size and weight of tumor tissues

The length, width and height of tumors are measured with a vernier caliper. And the tumor weight and size is calculated with the formula: size=$\pi/6\times$(length)$\times$(width)$\times$(height).

Figure 3:
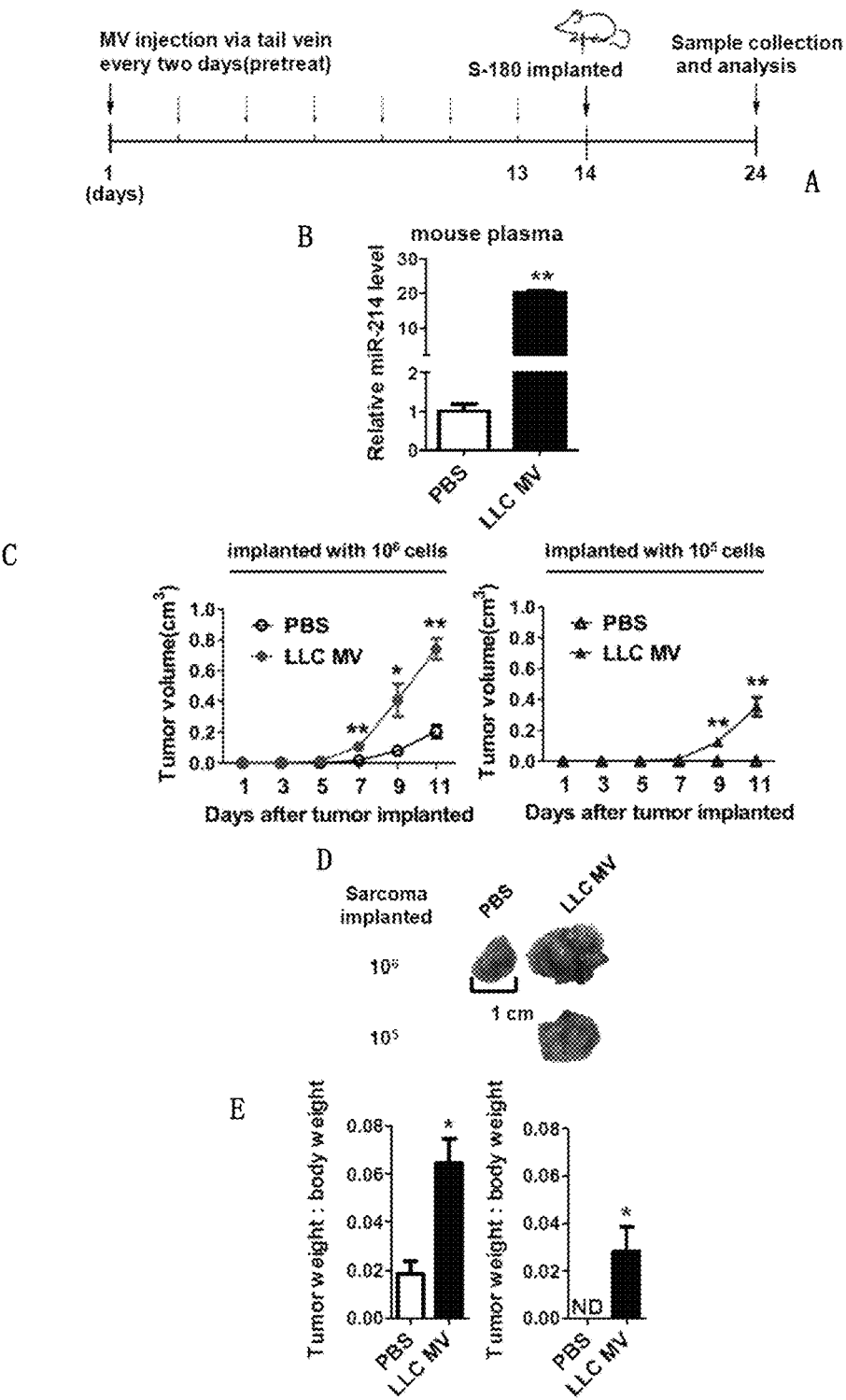
FIG. 3 shows the effect of LLC MVs on the growth of tumors. 'PBS' is the control group, 'LLC MV' is the test group.

The detailed results are shown in FIGS. 2 and 3.

In which, FIG. 2B shows the miR-214 expression in the plasma of mice intravenously injected with LLC MVs. 'PBS' represents the control. Being compared with the control group, the miR-214 expression in the plasma of the test group (LLC MV) is significantly increased.

FIG. 2C shows that the cell count of $CD4^+CD25^{high}Foxp3^+$ Tregs in the total peripheral blood of mice after being treated with LLC MVs is increased from 3.2% to 5.5%, in which 'PBS' represents the control group, and 'LLC MV' represents the test group.

FIG. 2D shows that the cell count of $CD4^+CD25^{high}Foxp3^+$ Tregs in the spleen $CD4^+$ cells of mice after being treated with LLC MVs is increased from 7.8% to 12.7%, in which 'PBS' represents the control group, and 'LLC MV' represents the test group.

FIG. 3B shows that, being compared with the control group, which is represented by the PBS group, the miR-214 expression in the plasma of the test group (LLC MV) is significantly increased. The miR-214 expression in the s-180 tumor transplant mice plasma pre-treated with LLC MVs is increased up to 20 times.

FIG. 3C shows that the implanted tumor is significantly enlarged after LLC MV treatment, with PBS pre-treatment as the control group, and LLC MV as the test group.

FIG. 3D shows that, with PBS pre-treatment as the control group, and LLC MV pre-treatment as the test group, when $10^5$ S-180 cells are implanted, the tumor of the control group mice does not grow, while that of the test group grows rapidly; when $10^6$ S-180 cells are implanted, the tumor of the test group grows more rapidly than that of the control group.

FIG. 3E shows that, with PBS pre-treatment as the control group, and LLC MV pre-treatment as the test group, being compared with that of the control group, the weight of tumor in the test group mice (LLC MVs pre-treatment) is significantly increased.

Example 3 Effect of miR-214 Free MVs on Treg Cells

Method: LLC cells originated miR-214 free MVs are obtained through knocking out the miR-214 in LLC cells with antisense oligonucleotide, and then collecting the MVs in nutrient solution; $CD4^+$ T cells in mice spleen are collected with Miltenyi $CD4^+$ Cell Isolation Kit (Miltenyi Biotec Co. Ltd., Germany) and then cultured; the $CD4^+CD25^{high}Foxp3^+$ cell count is detected with eBioscience Treg Flow Detection Kit (eBioscience Co. Ltd.) on a flow cytometry.

3.1 Culture of mice Lewis lung cancer cells (LLC cells) (Cell Bank, China Academy of Science)

The mice LLC cells (Cell Bank, China Academy of Science) are cultured in complete medium with high glucose DMEN, 10% FBS, 4 mmol/L glutamine and double antibody, in incubator with 5% $CO_2$.

3.2 The knock-out of miR-214 with anti-sense oligonucleotide

LLC cells are transplanted in 60 ml culture dish, and each dish is transfected with 300 pmol anti-miR-214 (Ambion), with anti-miRNA (anti-ncRNA, Ambion) as the negative control.

3.3 Preparation of LLC cells originated miR-214 free MVs

LLC cells are transfected with anti-miR-214 and anti-miRNA (anti-ncRNA) using liposomal transfection reagent following the instruction. After 6 hours, the culture medium is replaced with 1% MV knocked-out bovine serum DMEM. After 48 hours, the cell culture is collected and MVs are separated.

3.4 The collection and culture of mice $CD4^+$ T cells

Collection: spleen of mice (6-8 weeks) is freshly collected, grounded and pass through 200-mesh sieve, and prepared into single cell suspension; said suspension is separated with mice lymphocyte separation medium, and milky white lymphocytes therein are collected and washed twice with PBS; then the lymphocytes are labeled with Miltenyi $CD4^+$ Cell Isolation Kit (Miltenyi Biotec Co. Ltd., Germany) and sieved through magnetic columns, so that $CD4^+$ cells are separated and collected.

Culture conditions: the culture solution is formulated with RPMI 1640, 12% FBS, 4 mmol/L glutamine, 1 mmol/L HEPES, double antibody, in incubator with 5% $CO_2$.

Culture method: the final density of the collected $CD4^+$ T cells is adjusted to $10^6$ cells/ml. To activate the $CD4^+$ T cells, 1 µg/mL mice CD3e antibodies and 1 µg/mL CD28 are added into the culture solution.

3.5 Experiment groups

The control group: mice $CD4^+$ T cells of primary culture not treated with LLC MVs;

Test group 1: mice $CD4^+$ T cells of primary culture, treated with LLC MVs of 5 LLC MV (5 µs protein is added to every $10^5$ cells);

Test group 2: mice $CD4^+$ T cells of primary culture, treated with LLC MVs of 10 LLC MV (10 µs protein is added to every $10^{10}$ cells);

Test group 3: mice $CD4^+$ T cells of primary culture, treated with miR-214 knocked-out LLC MVs of 10 LLC MV/miR-214$^{def}$ (5 µs protein is added to every $10^5$ cells).

3.6 The $CD4^+CD25^{high}Foxp3^+$ cell count of mice in each group is detected with eBioscience Treg Flow Detection Kit (eBioscience Co., Ltd.) on a flow cytometry. The specific operation is as said in Example 1. The detailed results are shown in FIG. 4.

It can be seen in FIG. 4A that, Control represents the control group, 5 LLC MV, 10 LLC MV, 10 LLC MV/miR-214$^{def}$ are the test groups. Being compared with the control group, being treated with 5 LLC MV and 10 LLC MV, the CD4$^+$CD25$^{high}$Foxp3$^+$ cell count increases significantly; being treated with 10 LLC MV/miR-214$^{def}$, the CD4$^+$CD25$^{high}$Foxp3$^+$ cell count shows no significant change.

It can be seen in FIG. 4B that, 'control' represents the control group, '5 LLC MV', '10 LLC MV', '10 LLC MV/miR-214$^{def}$' represent the test groups. Being compared with the control group, being treated with 5 LLC MV and 10 LLC MV, the CD4$^+$CD25$^{high}$Foxp3$^+$ cell count increases significantly; being treated with 10 LLC MV/miR-214$^{def}$, the CD4$^+$CD25$^{high}$Foxp3$^+$ cell count shows no significant change.

Figure 4:
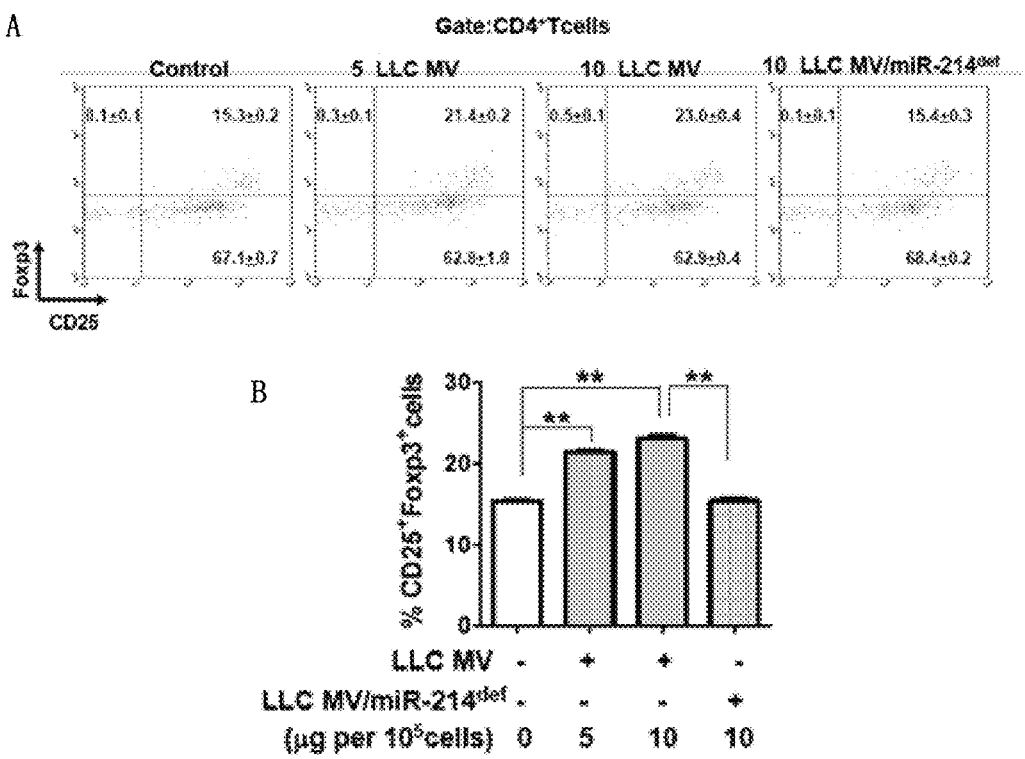
FIG. 4 shows induction effect in vitro into the $CD4^+$ $CD25^{high}Foxp3^+$ regulatory T cells on the $CD4^+$ T cells treated for 72 hours with LLC MVs or miR-214 deficient LLC MVs.

In summary, it can be seen from FIG. 4 that, the extragenous miR-214 (LLC MVs of different concentration, MVs containing miR-214) significantly up-regulates the content of CD4$^+$CD25$^{high}$Foxp3$^+$ regulatory T cells, while no significant effect can be placed on the increase of Tregs by miR-214 knocked-out MVs. The in vitro experiments validates that the Tregs increase is dependent on miR-214.

In which, FIG. 4A exhibits as a representative the data of 1 out of 5 flow experiment groups. Said 5 experiment groups are independent from each other, and the results marked in the figure is the mean value±Standard Error Mean (SEM).

Example 4 miR-214 Induces Treg Cells, and Anti-miR-214 is for Tumor Inhibition Methods 4.1 Experiment groups The control group: naked mice (Experiment Animals Center, Nanjing General Hospital) are treated with PBS;

Test group 1: naked mice, treated with CD4$^+$ T cells of primary culture;

Test group 2: naked mice, treated with CD4$^+$ T cells of primary culture that are pre-treated with LLC MVs (10 μg protein/10$^5$ CD4$^+$ T cells);

Test group 3: naked mice, treated with CD4$^+$ T cells of primary culture that are pre-treated with miR-214 knocked-out LLC MVs (10 μg protein/10$^5$ CD4$^+$ T cells).

The naked mice of test group 1-3 are injected via tail vein with CD4$^+$ T cells at the dose of 5×10$^6$ cells/mouse, and these of the control group are injected via tail vein with PBS.

4.2 The naked mice of test groups and the control group are hypodermically implanted with 10$^6$ sarcoma S-180 cells/mouse.

Samples are collected after 5 days.

The naked mice of test groups and the control group are observed to tell whether differences of tumor growth exist after the generation of T-reg induced by CD4$^+$ T celled treated with exogenous miR-214.

4.3 Detection of the size and weight of tumor tissues. The specific operation steps are as said in Example 2.

In all 4 groups are measured, and in each group n=6-8. The result is obtained through mean value±SEM.

Results

Figure 5A:
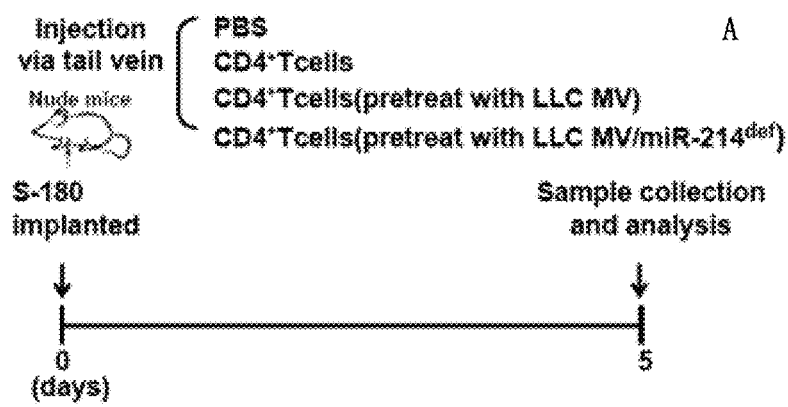
FIG. 5A is the experiment flow chart of example 4.

It can be seen in FIG. 5B that, PBS represents the control group, CD4$^+$ T, CD4$^+$ T (LLC MV), CD4$^+$ T (LLC MV/miR-214$^{def}$) are the test groups. Being compared with the control group, the tumor of the CD4$^+$ T (LLC MV) test group is significantly enlarged; while the tumor of the CD4$^+$ T and CD4$^+$ T (LLC MV/miR-214$^{def}$) is significantly diminished.

It can be seen that, being injected with CD4$^+$ T cells that have an up-regulated Treg content induced by exogenous miR-214, the tumors of naked mice are significantly larger than those of the control group, while those of naked mice injected with not treated CD4$^+$ T cells and miR-214 knocked-out LLC MVs are significantly smaller than those of the control group.

FIG. 5C shows the weight of tumors, which is consistent with that in FIG. 5B. Being compared with the control group, the tumor weight of CD4$^+$ T (LLC MV) test group is significantly increased; the tumor weight of CD4$^+$ T and CD4$^+$ T (LLC MV/miR-214$^{def}$) test groups is significantly decreased. It indicates that, being injected with CD4$^+$ T cells that have an up-regulated Treg content induced by exogenous miR-214, the tumors are significantly heavier than those of the control group, while those of mice injected with not treated CD4$^+$ T cells and CD4$^+$ T cells treated with miR-214 knocked-out LLC MVs are significantly lighter.

Conclusion

Tregs induced by tumor secreted miR-214 can significantly promote the growth of tumors implanted in mice, which proves that the tumor secreted miR-214 induced Tregs can significantly inhibit the immune response reaction of cytotoxic cells such as NK cells and macrophages, which can kill tumor cells.

Example 5 Tumor Cell Secreted, miR-214 Containing MVs Take Effect Through Treg Cells LLC MV/miR-214$^{def}$ refers to the MV, of which miR-214 is knocked-out, or miR-214 deficient MV.

5.1 Construction of Treg deficient (Foxp3$^{DTR}$) model mice

Foxp3$^{DTR}$ transgenetic mice can be used to construct Treg cells knocked-out mice. Due to that the Treg cells express diphtherotoxin receptors, the Treg cells of Foxp3$^{DTR}$ mice are knocked out with the diphtherotoxin treatment. The test group consists of Foxp3$^{DTR}$ mice, and the control, wild type Foxp3$^+$ mice (Model Animal Research Center of Nanjing University).

Treatment of Foxp3$^{DTR}$ mice and wild type (WT, Foxp3$^+$) mice with diphtherotoxin Foxp3$^{DTR}$ mice and wild type mice, which are littermates, are intraperitoneally injected for 6 consecutive days with diphtherotoxin, and the injection dose is calculated as 50 μg/kg.

Since diphtherotoxin does not diminish the Treg content in the control, Foxp3$^+$ mice, but does bring the Treg content down in a dose dependent way in the lymphonodus, peripheral blood, spleen and thymus of Foxp3$^{DTR}$ mice, the Treg cells of the latter are completely removed through the 6 days' treatment.

5.2 From the beginning of diphtherotoxin injection, the Foxp3$^{DTR}$ and wild type mice are injected via tail vein with miR-214 containing LLC MVs and miR-214 deficient LLC MV/miR-214$^{def}$ (100 μL PBS containing 20 μg protein MV). The treatment is made every other day, and for two consecutive weeks.

5.3 On the 10th day, the mice are hypodermically injected with S-180 sarcoma cells. And on the 17th day, they are sacrificed, and the samples thereof are collected.

5.4 The expression of plasma miR-214 in mice is detected with Real-time PCR. The specific operation steps thereof are as said in Example 1. The specific operation steps are as said in Example 1.

5.5 CD4$^+$ T cells in mice spleen are collected with Miltenyi CD4+ Cell Isolation Kit (Miltenyi Biotec Co. Ltd., Germany). The specific operation steps thereof are as said in Example 2. The specific operation steps are as said in Example 2.

5.6 The CD4$^+$CD25$^{high}$Foxp3$^+$ cell count of all groups is detected with eBioscience Treg Flow Detection Kit (eBioscience Co. Ltd.) on a flow cytometry. The specific operation steps thereof are as said in Example 2. The specific operation steps are as said in Example 2.

5.7 Measurement of tumor size. The specific operation steps are as said in Example 2.

The detailed results are shown in Table 1 and FIG. 6.

Results

As shown in FIG. 6B, the CD4$^+$ T cell miR-214 expression in the peripheral blood of littermate Foxp3$^{DTR}$ and wild type Foxp3$^+$ mice is significantly up-regulated after LLC MV injection, but remains unchanged after LLC MV/miR-214$^{def}$ injection.

As shown in FIG. 6C, on the 7th, 13th, 15th and 17th day of LLC MVs and LLC MV/miR-214 def treatment, being compared with the LLC MV/miR-214$^{def}$ treatment group, the Tregs content in the peripheral blood CD4$^+$ T cells of Foxp3$^+$ mice treated with LLC MVs is significantly up-regulated. Meanwhile, the Tregs content in the peripheral blood CD4$^+$ T cells of Foxp3$^{DTR}$ mice treated with LLC MVs and LLC MV/miR-214$^{def}$ is not affected.

As shown in FIG. 6D, the proliferation of sarcoma cells in Foxp3$^+$ mice treated with LLC MVs is more rapid than that in Foxp3$^+$ mice treated with MV/miR-214$^{def}$; the tumor growth in Foxp3$^{DTR}$ mice cannot be promoted by LLC MVs and LLC MV/miR-214$^{def}$ treatment.

Table 1 shows the relative expression of miR-214 in the peripheral blood CD4$^+$ T cells, the content of Treg CD4$^+$ T cells and tumor size of Foxp3$^{DTR}$ mice and wild type mice, treated with LLC MVs and LLC MV/miR-214$^{def}$. The results therein are consistent with FIG. 6.

TABLE 1

|  | LLC MV (extragenous miR-214) | LLC MV/miR-214$^{def}$ (miR-214 knocked-out) |
|---|---|---|
| Foxp3$^+$ (wild type) | miR-214 up-regulated Treg up-regulated Rapid tumor proliferation | miR-214 remains Treg remains Slow tumor proliferation |
| Foxp3$^{DTR}$ (Treg knocked-out) | miR-214 up-regulated Treg remains Tumor growth not promoted | miR-214 remains Treg remains Tumor growth not promoted |

Example 6 MiR-214 Inhibitor can Inhibit the Proliferation of Treg Cells

Method: n=6-8, with data obtained through mean value±standard error mean

Anti-miR-214 enriched MVs are obtained through transfecting anti-miR-214 (ASO) into 293T cells. As preparation, mice were implanted through axillary hypodermal injection with S-180 tumor cells; when the tumor size reached the average (diameter of around 0.6 cm) after one week's growth, the control, 293T derived MVs and the transformed 293T MVs/anti-miR-214 are injected to mice via tail vein, with 20 µg MV for each mouse at one time, and one injection on every other day. The specific chart is shown in FIG. 4-1. The mice are sacrificed after 14 days. The data are collected.

6.1 Construction of sarcoma S-180 implant mice. The specific operation steps are as said in Example 1. The specific operation steps are as said in Example 1.

6.2 293T cells are transfected with anti-miR-214 and then cultured. The supernatant of culture medium is collected and then separated for the anti-miR-214 enriched 293T MV/anti-miR-214. 293T cells are transfected with anti-ncRNA to produce 293T MV/anti-ncRNA with low miR-214 content.

6.3 Experiment groups

Control group 1: mice not transplanted with sarcoma S-180;

Control group 2: mice transplanted with sarcoma S-180, injected via tail vein with PBS (100 µl PBS) every 2 days, beginning on the 7th day;

Test group 1: mice transplanted with sarcoma S-180, injected via tail vein with 293TMV/anti-ncRNA (20 µg protein MV, 100 µl PBS) every 2 days, beginning on the 7th day;

Test group 2: mice transplanted with sarcoma S-180, injected via tail vein with 293TMV/anti-miR-214 (20 µg protein MV, 100 µl PBS) once every 2 days, beginning on the 7th day.

The MV treatment is made once every 2 days for 2 weeks. On the 21st day, samples are collected.

6.4 CD4$^+$ T cells collected with Miltenyi CD4$^+$ Cell Isolation Kit (Miltenyi Biotec Co. Ltd., Germany). The specific operation steps thereof are as said in Example 2. The specific operation steps are as said in Example 2.

6.5 The CD4$^+$CD25$^{high}$Foxp3$^+$ cell count in the mice of each group is detected with eBioscience Treg Flow Detection Kit (eBioscience) on a flow cytometry. The specific operation steps thereof are as said in Example 2. The specific operation steps are as said in Example 2.

6.6 Detection of the size and weight of tumor tissues. The specific operation steps are as said in Example 2.

Results

As shown in FIG. B-C, compared with the control group not implanted with sarcoma s-180 (PBS) and the sarcoma s-180 model mice treated with PBS (PBS), the Tregs count in the whole blood (B1) and spleen (C1) of sarcoma s-180 model mice injected with 293T MV/anti-miR-214 (293TMV/anti-miR-214) is significantly down-regulated; while the CD4+ T cells count in the whole blood (B1) and spleen (C1) of sarcoma s-180 model mice injected with 293T MV/anti-ncRNA (293T MV/anti-ncRNA) shows no significant change. It can thereby be seen that, anti-miR-214 ASOs can successfully inhibit the proliferation of CD4$^+$ CD25$^{high}$Foxp3$^+$ Tregs.

Besides, as shown in FIG. 7D-F, compared with the control group not implanted with sarcoma s-180 (PBS) and the sarcoma s-180 model mice treated with PBS (PBS), the growth speed, volume and weight of tumor in sarcoma s-180 model mice injected with 293T MV/anti-miR-214 (293TMV/anti-miR-214) is significantly down-regulated, while growth speed, volume and weight of tumor in sarcoma s-180 model mice injected with 293T MV/anti-ncRNA (293TMV/anti-ncRNA) shows no significant change.

Conclusion: the results above prove that, delivery of anti-miR-214 ASOs with MVs is an effective means to inhibit the proliferation of tumor induced Tregs proliferation and the growth of implanted tumor. The tumor secreted miR-214 transforms CD4$^+$ T cells into immune inhibitory Treg cells and thereby promotes tumor evasion.

All the documents mentioned in the present invention are incorporatedly referred to, as well as each alone. In addition, it should be understood that after reading the teachings of the present invention described above, a skilled person in the art can make various changes or modifications of the invention, and these equivalent forms shall also fall into the scope of the present application as defined by the appended claims.

The invention claimed is:

1. A method for treating sarcoma or lung cancer by administering a safe and effective dose of microvesicles to a subject in need thereof so as to treat the sarcoma or lung cancer by inhibiting Treg cells, wherein said microvesicles contain a miRNA-214 inhibitor which is an anti-sense nucleotide sequence of miRNA-214 or a precursor thereof.

2. The method according to claim 1, wherein said Treg cells include CD4+ CD25+ Treg, CD4+ Th3, CD4+ Tr1, CD4+ CD25+ Treg, or CD4+ CD8+ Ts.

3. The method according to claim 1, wherein said miRNA-214 inhibitor further inhibits immune evasion of said sarcoma or lung cancer.

4. The method according to claim 1, wherein said inhibiting Treg cells comprises inhibiting differentiation of T cells into Treg cells, growth of Treg cells, or reproduction of Treg cells.

5. The method according to claim 1, wherein said inhibiting Treg cells is inhibiting differentiation of T cells into Treg cells or growth of Treg cells.

6. The method according to claim 1, wherein said microvesicles are obtained through transfecting said anti-sense nucleotide sequence of miRNA-214 or the precursor thereof into 293T cells.

7. The method according to claim 1, wherein said Treg cells include $CD25^+$ $Foxp3^+$ Treg cells.

* * * * *